United States Patent [19]

Hayden

[11] Patent Number: 5,542,422
[45] Date of Patent: Aug. 6, 1996

[54] SYSTEM AND METHOD FOR DETECTING CATARACTOGENESIS USING QUASI-ELASTIC LIGHT SCATTERING

[75] Inventor: Douglas L. Hayden, Cambridge, Mass.

[73] Assignee: Oculon Corporation, Cambridge, Mass.

[21] Appl. No.: 328,901

[22] Filed: Oct. 25, 1994

[51] Int. Cl.⁶ .................................................... A61B 3/10
[52] U.S. Cl. .................... 128/633; 128/653.1; 128/665
[58] Field of Search ..................................... 128/632, 633, 128/653.1, 664, 665, 745; 351/200, 205, 214, 221

[56] References Cited

U.S. PATENT DOCUMENTS

| | | | |
|---|---|---|---|
| 4,702,576 | 10/1987 | Magnante | 128/633 |
| 4,957,113 | 9/1990 | Benedek | 128/665 |
| 4,993,827 | 2/1991 | Benedek et al. | 351/221 |
| 5,072,731 | 12/1991 | Taratuta et al. | 128/633 |
| 5,279,296 | 1/1994 | Thurston et al. | 128/653.1 |

*Primary Examiner*—Krista M. Zele
*Attorney, Agent, or Firm*—Seed and Berry LLP

[57] ABSTRACT

A new model autocorrelation function is provided to which autocorrelation data is fit. The model function is empirically derived based on previously collected autocorrelation data and is indicative of the degree of cataractogenesis. The model autocorrelation function contains five parameters to characterize first and second portions of a fitted curve. In one embodiment, the model autocorrelation function has a single exponential and a single second order polynomial component to represent the first and second portions of the fitted curve, respectively. In an alternative form, the square root of the autocorrelation function is used as the model with the square root form being linear in four of five terms. The linearity in four of five terms permits the fitting of the data points to the model function using simple linear regression analysis. Other forms of mathematical models, such as a straight line first portion and a parabolic second portion may use five parameters to model the autocorrelation data.

18 Claims, 7 Drawing Sheets

Fit 129 points with 'ocu.5'
Double exponential heterodyned model, version 5.2
Instrumental weights
Converged by $\varepsilon$ test ($\varepsilon$ = 0.001)
$10 \leq x \leq 1280$

| | |
|---|---|
| $\chi^2$ = 1.231e-06 | $\chi^2 I^2$ = 0.0126 |
| base = 0 | Intens = 101 |
| f = 0.0562±0.001 | ResAveMax = 0.0041 |
| tau_f = 75±15 | DurWatStat = 2 |
| amp_s = 0.781±0.036 | Lens = |
| tau_s = 4.4e+03±1.2e+03 | Loc = |
| amp_i = 0.624±0.058 | calculated baseline for fit |

```
F  = 0.1537              Visit = 1.
As = 0.9747              Standard = -1
τf = 139.9               Lens = os
C1 = -8.823e-6           Location = n
C2 = 7.784e-12           Delayed baseline = 794579
                         Intensity = 223.9
                         Inclusion = y
```

B0 = 0.3185
B1 = -7.026e-6
B2 = 3.48e-10
B3 = 0.02163
$\tau_f$ = 205.2

Visit = 1
Standard = -1
Lens = os
Location = a
Delayed baseline = 195993
Intensity = 110.6

```
B0 = 0.3515                  Visit = 0
B1 = -3.959e-6               Standard = -1
B2 = 6.065e-11               Lens = os
B3 = 0                       Location = a
τf = 1.                      Delayed baseline = 325279
                             Intensity = 141.2
```

B0 = 0.2617
B1 = -3.069e-6
B2 = -1.577e-10
B3 = 0
$\tau_f$ = 1.

Visit = 1
Standard = -1
Lens = od
Location = n
Delayed baseline = 11079400
Intensity = 832.6

Fig. 7C

SYSTEM AND METHOD FOR DETECTING CATARACTOGENESIS USING QUASI-ELASTIC LIGHT SCATTERING

TECHNICAL FIELD

The present invention relates generally to a system and method for detecting cataractogenesis using quasi-elastic light scattering, and more particularly, to a system and method for fitting data points to a new curve fitting model.

BACKGROUND OF THE INVENTION

A reliable, quantitative method for the measurement of molecular changes associated with early cataractogenesis has long been an important goal of human clinical cataract research. Such a method would allow researchers and physicians to (a) assess the effectiveness of anticataract drugs; (b) determine the effects of pharmacological agents or radiation used in the treatment of systemic diseases on the formation of cataracts; and (c) provide a quantitative basis for the medical decision to intervene surgically or pharmaceutically in the treatment of cataract.

In recent years quasi-elastic light scattering (QLS) has been used to study the ocular lens in vivo and in vitro. A method and apparatus for analyzing QLS is described in U.S. Pat. Nos. 4,957,113, and 5,072,731, respectively, which are incorporated herein by reference.

The techniques described in the above-referenced patents are capable of quantitatively measuring the amount of light scattered by diffusing chemical species in a medium, as well as their rates of diffusion. With QLS, the time fluctuations in intensity of light scattered by a selected small volume in the lens which is illuminated by an incident laser beam are studied. The scattered light intensity fluctuates in time because of the Brownian motion of the scattering elements. Brownian motion is defined as the motion of macromolecules caused by thermal agitation and the random striking by neighboring molecules in a solution. In the lens of the human eye, the Brownian motion of protein molecules may be recorded and analyzed by quasi-elastic light scattering.

Research has shown that the principal scattering elements within the lens are the molecular constituents of the fiber cells. These constituents are principally globular proteins called crystallins. The aggregation of small proteins within the lens is the very first stage in the process of cataractogenesis. As the light scattering becomes more pronounced, it becomes noticeable to the clinician and is termed a cataract. However, this represents a late stage of a continuous process of increase in light scattering with time within the lens. By using information obtained from the light scattered by the various fast and slow moving protein species, it is possible to determine the degree of aggregation and thus the degree of cataractogenesis before it would be noted clinically.

The intensity fluctuations of the scattered light are detected by collecting the light scattered from the illuminated volume in the eye lens and focusing this light onto the surface of an optical detector such as a photomultiplier tube or solid-state photodiode. The output of the detector is a photoelectric current whose temporal fluctuations are synchronized with the fluctuations in the scattered light intensity. The temporal fluctuations in the photoelectric current can be mathematically analyzed to provide a quantitative measure of the degree of cataractogenesis.

The experimental data is typically expressed in the form of the temporal autocorrelation function, $C(\tau)$, of the intensity of the detected scattered light from the scattering medium as a function of the delay time, $\tau$. From the mathematical form of the autocorrelation function, it is possible to determine the diffusivity of the scattering elements undergoing Brownian movement. The collected data is fit to a model autocorrelation function. The fitted parameters of the model autocorrelation function have been shown clinically to provide an accurate quantitative measure of the source of increased light scattering on a molecular level long before cataract formation could be detected visually by either the subject or the physician.

The QLS inventions described in the above-referenced patents have provided tools to detect cataract formation at a very early stage. However, the research instruments of the prior art are not always efficient from the clinical perspective. A practical clinical instrument must perform the QLS measurements quickly and accurately. Data must be collected quickly to minimize patient discomfort and to minimize effects of artifact such as patient eye movement. For this reason, a small number of data points collected over a relatively brief period of time must provide the desired information. The curve fitting routine must accurately fit the model autocorrelation function and provide the physician with reliable results from which to make a diagnosis. If there are too few parameters in the model autocorrelation function, then certain characteristics in the data will not be analyzed. If there are too many parameters in the model autocorrelation function, then the parameters will be statistically interdependent and may have diminished meaning when interpreting data. Therefore, it can be appreciated that there is a significant need for a method and apparatus for detecting cataractogenesis that is applicable to clinical situations. The present invention fulfills this need and provides other related advantages.

SUMMARY OF THE INVENTION

The present invention is embodied in a system for the in vivo inspection of ocular tissue that comprises a light source producing a light, an optical system to deliver the light to the ocular tissue, and a collection optical system to collect light scattered by the ocular tissue. A light detector generates signals corresponding to an intensity of the collected scattered light. An analyzer coupled to the light detector analyzes the signals and generates a plurality of data points corresponding to the intensity of the light scattered by scattering elements within the ocular tissue. A curve fitter fits the plurality of data points to a predetermined model representative of a light scattering process within the ocular tissue. The curve fitter generates a fitted curve having five parameters representing the plurality of data points.

In one embodiment the fitted curve has first and second portions with the predetermined model having an exponential term representing the first portion and a polynomial term representing the second portion. The exponential term can have the following form:

$$(1-A_s)*e^{-\tau/\tau_f}$$

where $A_s$ is a coefficient representative of the cumulative effect of light scattered from slowly diffusing scatterers, immobile scatterers, and elements that give rise to nonexponential characteristics within the measurement volume, $\tau$ is a time delay variable, and $\tau_f$ is inversely proportional to the diffusivity of fast diffusing mobile scatterers.

The polynomial term may have the following form:

$$A_s * (1 + C_1 * \tau + C_2 * \tau_2)$$

where $\tau$ is a time delay variable, and $A_s$, $C_1$, and $C_2$ are coefficients that represent the cumulative effect of light scattered from slowly diffusing scatterers, immobile scatterers, and elements that give rise to nonexponential characteristics within the ocular tissue.

In an alternative embodiment, the first portion can be modeled by a portion of a straight line and the second portion can be modeled by a portion of a parabola.

DETAILED DESCRIPTION OF THE INVENTION

Figure 1:
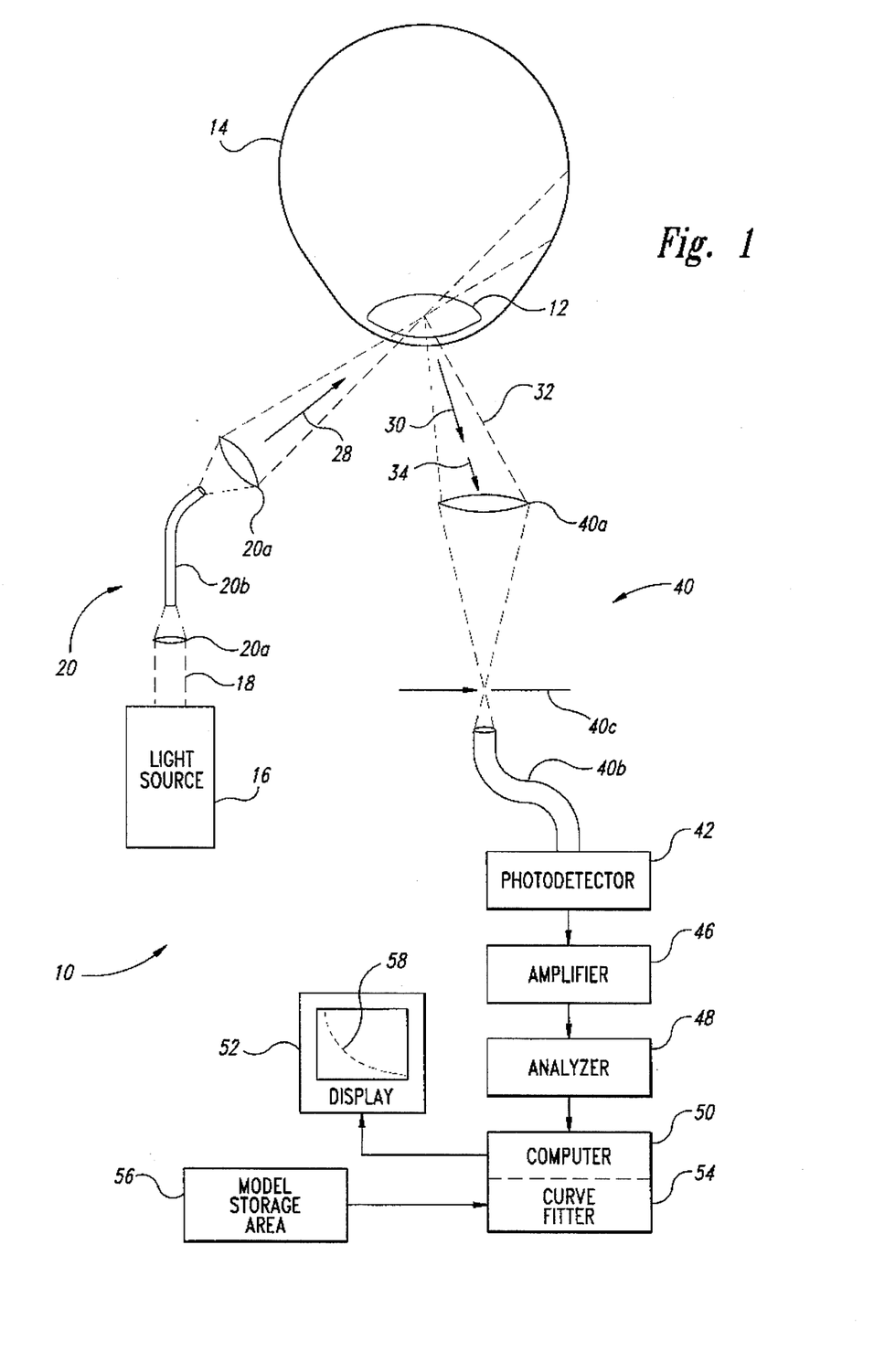
FIG. 1 is a schematic representation of an optical scattering analyzer for the study of light scattered in vivo from the lens of a subject.

The present invention provides an improved apparatus and method for detecting cataractogenesis. A preferred embodiment of the present invention is reflected in an apparatus shown in schematic form in FIG. 1. Referring to FIG. 1, an optical scattering analyzer 10 is used for the study of light scattered in vivo from a lens 12 of an eye 14 of a subject. A light source 16 produces a monochromatic, coherent, collimated light beam 18 of wavelength in the visible range. In the presently preferred embodiment, the light source 16 is a helium-neon laser having a wavelength of 632.8 nanometers (nm). However, those skilled in the art will recognize that any light source 16 in the visible spectrum or above, whether monochromatic, coherent, and/or collimated, or not, will work with the system 10. The present invention is not limited by the specific wavelength of the light source 16.

Figure 2:
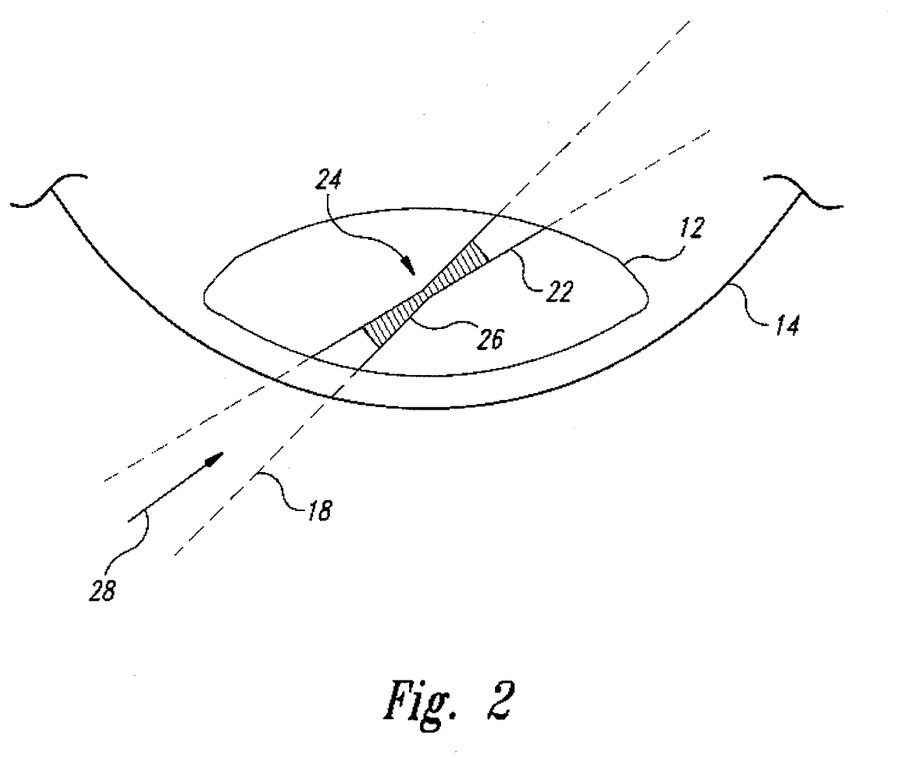
FIG. 2 is a schematical cross-sectional view of the human lens.

The light beam 18 is attenuated through conventional optics 20 so as to provide for two incident intensities: one is a maximum intensity of 200 microwatts used for measurement of the autocorrelation function, and the other is a maximum intensity of 40 microwatts used for alignment purposes between measurements. The optics 20 may include one or more conventional optical lens 20a and fiber optics 20b to focus the light beam 18 and deliver it to a desired location within the lens 12. The light beam 18 illuminates a volume 22 within the lens 12, as shown in FIG. 2. The optics 20 focuses the light beam 18 to a waist 24 having an approximate diameter of 15–60 microns. Returning again to FIG. 1, the light beam 18 is fixed so as to result in a backscattering angle of approximately 140 degrees between a direction 28 of propagation of the light beam onto the lens 12 and a direction 30 of propagation of scattered light 32 that is scattered by the lens. Each measurement of the autocorrelation function is conducted within a 5–10 second period. The resulting radiation is well within the guidelines of the American National Standards Institute for ocular exposure. It should be noted that other wavelengths for the light source 18 may permit longer exposure periods without damaging the lens 12.

A measurement optical path 34 coincides with the direction 30 of propagation of the scattered light 32. Within the measurement optical path 34, the scattered light 32 is collected by conventional optics 40. The conventional optics may include one or more conventional lens 40a, fiber optics 40b, and an optical aperture 40c. The optical aperture 40c limits the detected scattering to scattered light originating from a portion 26 of the volume 24 (see FIG. 2) which is approximately 200 microns in length in the lens 12. The portion 26 of the volume 22 from which scattered light is detected is referred to herein as a measurement volume. The optics 40 focuses the scattered light 32 on a photodetector 42. The photodetector 42 may be a photon-counting photomultiplier tube, such as one manufactured by Hamamatsu, a photodiode, or the like. The photodetector 42 produces a train of electrical pulses corresponding to the detection of photons. An amplifier-discriminator 46, such as one manufactured by Malvern Instruments, prepares the electrical pulses produced by the photodetector 42 for input to an analyzer 48. The analyzer 48 may be a power spectrum analyzer or an autocorrelator. In the presently preferred embodiment of the system 10, the analyzer 48 is an autocorrelator performing a temporal autocorrelation of the data.

The function of the analyzer 48 is to interrelate the intensity of the detected scattered light as a function of the delay time, $\tau$. The specific operational details of the analyzer 48, such as delay time, number of autocorrelation channels, and the like, is well known to those of ordinary skill in the art and need not be discussed herein. The analyzer 48 may be a standalone autocorrelator, such as one manufactured by Malvern, or incorporated into a computer 50. A display 52 coupled to the computer 50 permits the display of data.

A curve fitter 54 within the computer 50 fits the autocorrelation data to a model autocorrelation function stored within a model storage area 56. The model storage area 56 may be a part of a memory (not shown) of the computer 50 or a separate memory. The output of the curve fitter 54 is a fitted curve 58, which may be displayed on the display 52. The precise shape of the fitted curve 58 is determined from fitting the autocorrelation data to the model autocorrelation function. Curve fitting routines attempt to adjust the parameters of the model autocorrelation function to provide a best fit to the data points.

Figure 3A:
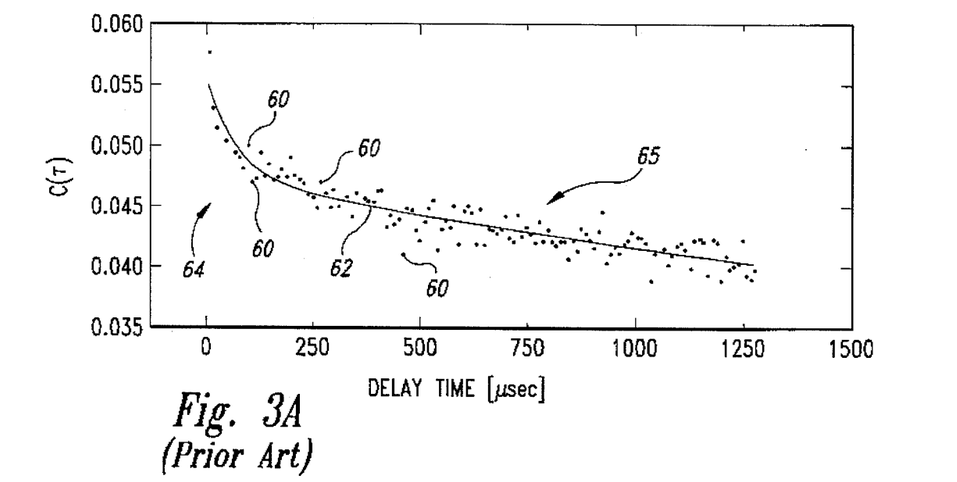
FIG. 3A is a graph of the data taken from a human lens in vivo using an autocorrelation function model of the prior art.
Figure 3B:
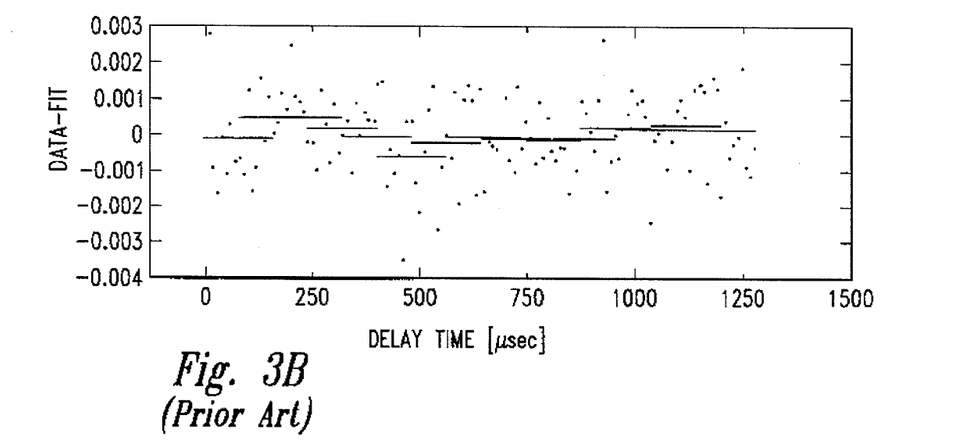
FIG. 3B is a graph of the residual data resulting from the curve fitting of the data of FIG. 3A to the autocorrelation function of the prior art.
Figure 3C:
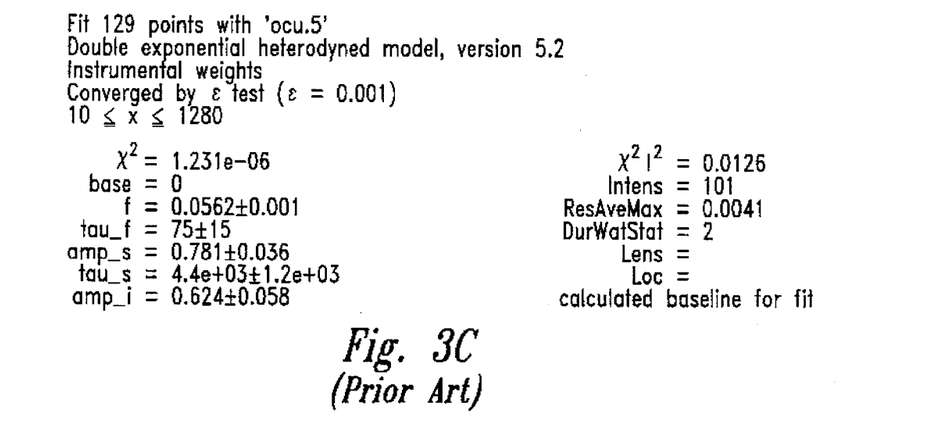
FIG. 3C illustrates the values of the parameters resulting from the curve fitting of the data of FIG. 3A to an autocorrelation function of the prior art.

As seen in FIG. 3A, the autocorrelation function is represented by a series of discrete data points 60. A fitted curve, $C_{fit}(\tau)$, indicated by the reference numeral 62, representing the autocorrelation model function, is determined by a curve fitting program. The fitted curve 62 has a first portion 64, representative of the intensity of light scattered by fast diffusing scatterers, and a second portion 65 of the fitted curve 62 representative of the intensity of light scattered by slow diffusing scatterers, immobile scatterers, and elements that give rise to nonexponential characteristics within the measurement volume 26. A more detailed discussion of nonexponential characteristics within the measurement volume 26 is provided below. Prior art systems generally employ a curve fitting algorithm such as the Marquardt nonlinear least squares algorithm to fit the discrete data points 60 to the model autocorrelation function.

U.S. Pat. Nos. 4,957,113, and 5,072,731, respectively, describe an apparatus and method for analyzing QLS data. The data detected by the apparatus is analyzed to determine a signature that is indicative of the degree of cataractogenesis in an individual subject. Subsequent patents and patent applications have described various elements of the signature and have determined additional components of the signature that can be used to determine the degree of cataractogenesis.

For example, in U.S. patent application Ser. No. 948,273, filed Sep. 21, 1992, and incorporated herein by reference, it is reported that the cataractogenesis signature can be further determined with the use of a dimensionless parameter, $F_{mos}$, which denotes the fraction of light intensity scattered by mobile scatterers which is associated with slowly moving scatterers. From this application, the model autocorrelation function has the following form:

$$C_N(\tau) = \alpha \left[ (1 - F_{mos}) e^{-\frac{\tau}{\tau_f}} + F_{mos} e^{-\frac{\tau}{\tau_s}} \right]^2 \quad (1)$$

where $C_N(\tau)$ is a normalized autocorrelation function, the term $\alpha$ denotes the observed amplitude to baseline ratio, $\tau_f$ and $\tau_s$ are time constants that characterize the rapidly and slowly diffusing scatterers, respectively, and $F_{mos}$ denotes the fraction of light scattered by mobile scatterers that is associated with slowly diffusing scatterers.

A subsequent patent, U.S. Pat. No. 5,279,296, incorporated herein by reference, reports that light scattering is due to both slow and fast diffusing proteins and is also due to immobile scatterers that do not diffuse at all. In that patent the in vivo detection of cataractogenesis is performed by collecting light from the ocular tissue and determining a signature of cataractogenesis therefrom. The signature includes the intensity of light scattered by immobile scatterers in the ocular tissue by treating the immobile scatterers as a constant in the model autocorrelation function, such that the model autocorrelation function has the following functional form:

$$C(\tau) = \alpha_0 [I_{mof} e^{-\tau/\tau_f} + I_{mos} e^{-\tau/\tau_s}]^2 + [I_{mof} + I_{mos} + I_{imm}]^2 \quad (2)$$

where $\tau$ is a time delay variable, $\tau_0$ is a constant representative of scattering in the absence of immobile particles, $I_{mof}$ is the intensity of light scattered by fast diffusing proteins, $I_{mos}$ is the intensity of light scattered by slow diffusing proteins, $\tau_f$ and $\tau_s$ are inversely proportional to the diffusion rates for fast and slow diffusing proteins, respectively, and $I_{imm}$ is the intensity of light scattered by immobile proteins.

Another patent application, U.S. patent application Ser. No. 149,353, filed Nov. 9, 1993, and incorporated herein by reference, further refines the use of immobile scatterers in the signature of cataractogenesis. The immobile scatterers are treated as other scattering elements in that there is a time dependence to the term representing the intensity of light scattered by immobile scatterers. The model autocorrelation function in U.S. patent application Ser. No. 149,353 has the following form:

$$C(\tau) = \alpha [I_{mof} e^{-\tau/\tau_f} + I_{mos} e^{-\tau/\tau_s} + I_{imm}]^2 + [I_{tot}]^2 \quad (3)$$

where $\tau$ is a time delay variable, $\alpha$ represent the amplitude to baseline ratio, $I_{mof}$ is the intensity of light scattered by fast diffusing proteins, $I_{mos}$ is the intensity of light scattered by slow diffusing proteins, $I_{imm}$ is the intensity of light scattered by immobile proteins, $\tau_f$ and $\tau_s$ represent diffusion rates for fast and slow diffusing proteins, respectively, and $I_{tot}$ denotes the total, average intensity of scattered light.

The previous work described above determines a cataractogenesis signature using the following general form of a double exponential autocorrelation function:

$$C_N(\tau) = \alpha \left( \Sigma F_i e^{-\frac{\tau}{\tau_i}} \right)^2 \quad (4)$$

where $C_N(\tau)$ is a normalized autocorrelation function, $\alpha > 0$ is the observed amplitude to baseline ratio, $0 \leq F_i \leq 1$ represents the fraction of light intensity scattered by each mobile diffusing species, $i$, and $\tau_i > 0$ are the time constants that characterize the mobile scatterers. In equation (4), it is understood that the sum of all $F_i$ equals 1. It is evident that $C_N(\tau)$, as given in equation (4) above, must satisfy the following equation:

$$\frac{d^2 C_N}{d\tau^2} > 0 \quad (5)$$

over all finite ranges of delay times.

Further research, described in U.S. patent application Ser. No. 149,209, filed Nov. 8, 1993, and incorporated herein by reference, indicated that there are non-double exponential components to the model autocorrelation function causing at least a portion of the autocorrelation data to have a curvature less than or equal to zero. The non-double exponential is characterized in one embodiment by a cosine term. The cosine term is used to account for changes in scattering elements within the measurement volume 26 (see FIG. 2) that may be caused by patient eye movement or by scattering elements that move in and out of the measurement volume 26 (see FIG. 2) during the course of the measurement. The system in U.S. patent application Ser. No. 149,209 describes a model autocorrelation function having the following form:

$$C(\tau) = \alpha B[(1 - F_{mos}) e^{-\tau/\tau_f} + F_{mos} e^{-\tau/\tau_s}]^2 + H^* \cos(2\pi\tau/\tau_c) + B \quad (6)$$

where $\alpha$ is an amplitude to baseline ratio of the exponential term, $F_{mos}$ is a dimensionless parameter denoting the fraction of light intensity scattered by mobile scatterers associated with slowly moving scatterers, $\tau$ is a time delay variable, $\tau_f$ is a diffusion time for fast diffusing scatterers, $\tau_s$ is a diffusion time for slow diffusing scatterers, H is an amplitude parameter of the nonexponential term, $\tau_c$, which is in units of time, represents the period of the cosine term and characterizes the correlation time of the nonexponential term, and B is a baseline value.

Equation (6) may be generalized to the following form:

$$C_N(\tau)=f*\{a_i+(1-a_i)*[(1-a_s)*e^{-\tau/\tau_f}+a_s*e^{-\tau/\tau_s}]\}^2 + h*\cos(2\pi\tau/\tau_c) \quad (7)$$

where f is the amplitude to baseline ratio of the exponential term, $a_i$ is the fraction of intensity of scattered light due to immobile scatterers, $a_s$ is the fraction of intensity of scattered light due to mobile scatterers which are slowly diffusing, $\tau$ is a time delay variable, $\tau_f$ is inversely proportional to the diffusivity of fast scatters, $\tau_s$ is inversely proportional to the diffusivity of slow scatters, h is the amplitude of the oscillatory component, and $\tau_c$ is the period of the oscillatory component.

Each of the previously discussed patents or pending applications further refines the signature of cataractogenesis to provide additional information, or a more accurate measurement for a larger segment of the population. Each of the signatures described in referenced patents or pending patent applications derived the model autocorrelation function based on an increased knowledge of the process of cataractogenesis. As can be seen from equation (7), there are seven parameters that must be adjusted to fit the autocorrelation data to the model autocorrelation function. Each of these seven parameters, f, $a_i$, $a_s$, $\tau_f$, $\tau_s$, h, and $\tau_c$, represent some physical and/or physiological process that causes light scattering in the lens 12 (see FIG. 1). For example, the fast and slow diffusion constants, $\tau_f$ and $\tau_s$ in equation (7) are inversely proportional to the rate of diffusion of fast and slow diffusing particles in the lens 12, respectively. Scattering elements are distributed within the lens 12 (see FIG. 1) in a non-homogeneous manner, which is referred to herein as spatial heterogeneity. The parameter h in equation (7) represents the fraction of the intensity of light scattered by scattering elements that, in part, because of the spatial heterogeneity of the lens 12, significantly affect the scattered intensity and its fluctuations when they move in and out of the measurement volume 26 (see FIG. 2) during the measurement period. Thus, the model autocorrelation functions of the prior art have their origin in the physics of the underlying process.

The various underlying physical and physiological processes result in seven parameters, however, the fitted curve 62 (see FIG. 3A) is "overdetermined" by the seven parameters of equation (7). The term overdetermined refers to the fact that the analyzer 48 produces the discrete data points 60 in such a fashion that the fitted curve 62 does not have sufficient variation to need representation by seven parameters. For example, the second portion 65 of the fitted curve 62 is affected by slow diffusing scatterers, immobile scatterers, as well as the elements that give rise to nonexponential characteristics within the measurement volume 26. In a clinical setting, it is not feasible to collect data for a long period of time so that the contribution to the model autocorrelation function of each of these parameters can be determined. In such circumstances, the seven parameters become highly correlated. This means that the selection of a particular value for one parameter by the Marquardt least-squares curve fitting algorithm will affect the value selected for another, supposedly independent, parameter. As a result, the fitted curve 62 (see FIG. 1) is more difficult to interpret.

The present invention is directed to a new form of model autocorrelation function that is derived from an empirical analysis of measured data rather than an analysis of the underlying physical and physiological processes. Nevertheless, the parameters derived from the empirical analysis can be used to interpret the underlying physical and/or physiological processes. The importance of deriving the model autocorrelation analysis from empirical analysis of the data is that many models can be applied to the discrete data points 60 (see FIG. 3A) to represent the various portions of the fitted curve 62.

Empirical analysis of discrete data points 60 and the resultant fitted curve 62 indicate the fitted curve may be represented by five parameters. The model autocorrelation function of the present invention contains only five parameters which are fitted to the discrete data points 60. This allows an accurate fit to all observed autocorrelation functions without the ambiguity inherent in overdetermining the fitted curve 62. The model autocorrelation function of the present invention is shown in the following equation:

$$C_N(\tau)=F*\{(1-A_s)*e^{-\tau/\tau_f}+A_s*(1+C_1*\tau+C_2*\tau^2)\}^2 \quad (8)$$

where $C_N(\tau)$ is the normalized autocorrelation function, F is an amplitude to baseline ratio, $\tau$ is a time delay variable, $\tau_f$ is inversely proportional to the diffusivity of fast scatterers, and $A_s$, $C_1$, and $C_2$ are coefficients that represent the cumulative effect of light scattered from slowly diffusing scatterers, immobile scatterers, and the elements that give rise to nonexponential characteristics within the measurement volume 26. The five parameters correspond to the intensity from fast diffusing scatterers, slow diffusing scatterers and immobile scatterers, as well as the nonexponential components discussed above in U.S. patent application Ser. No. 149,209.

Figure 4A:
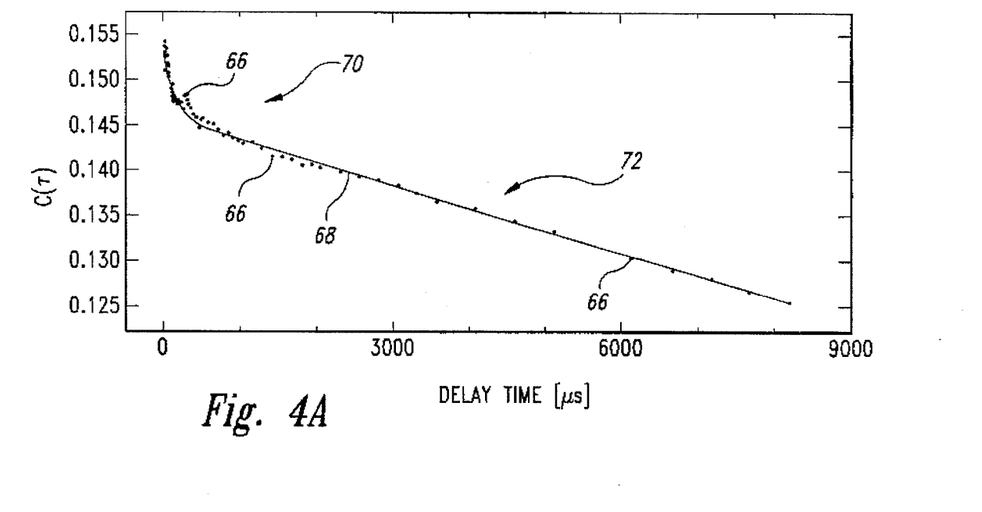
FIG. 4A is a graph of the data using the instrument of FIG. 1 taken from a human lens in vivo.

An example of the operation of the curve fitter 54 (see FIG. 1), using the model autocorrelation function of equation (8), is illustrated in FIG. 4A. In FIG. 4A, discrete data points 66 are fitted to a fitted curve 68 using the functional form of equation (8). The first term in equation (8), $(1-A_s)*e^{-\tau/\tau_f}$, represents a first portion 70 of the fitted curve 68. The first portion 70 of the fitted curve 68 represents the contribution to the intensity of light scattered by fast-diffusing scatterers within the lens 12 (see FIG. 1). The second order polynomial term in equation (8), $(1-A_s)*(1+C_1*\tau+C_2*\tau^2)$, represents a second portion 72 of the fitted curve 68. The second portion 72 of the fitted curve 68 represents the cumulative effect of light scattered from slowly diffusing scatterers, immobile scatterers, and elements that give rise to nonexponential characteristics.

Figure 4B:
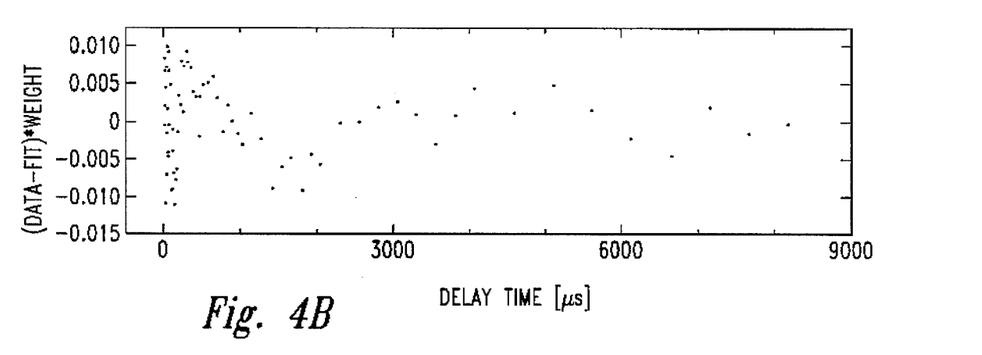
FIG. 4B is a graph of the residual data resulting from the curve fitting of the data of FIG. 4A to one embodiment of the model autocorrelation function of the present invention.
Figure 4C:
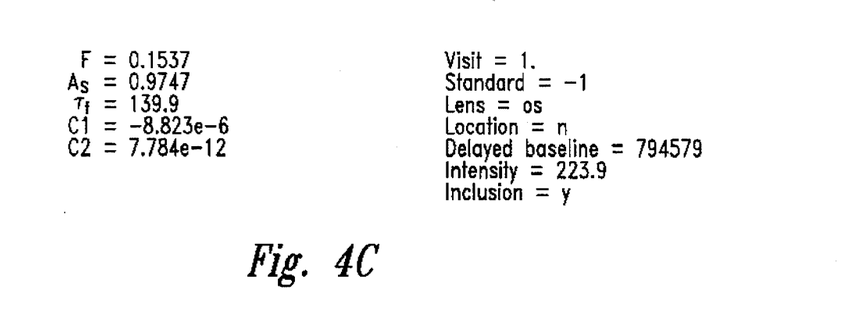
FIG. 4C illustrates the values of the parameters resulting from the curve fitting of the data of FIG. 4A to the inventive model autocorrelation function.

The residual data are plotted in FIG. 4B. FIG. 4C provides actual values for the live parameters to generate the fitted curve 68 from the discrete data points 66 using the model autocorrelation function of equation (8).

Figure 5A:
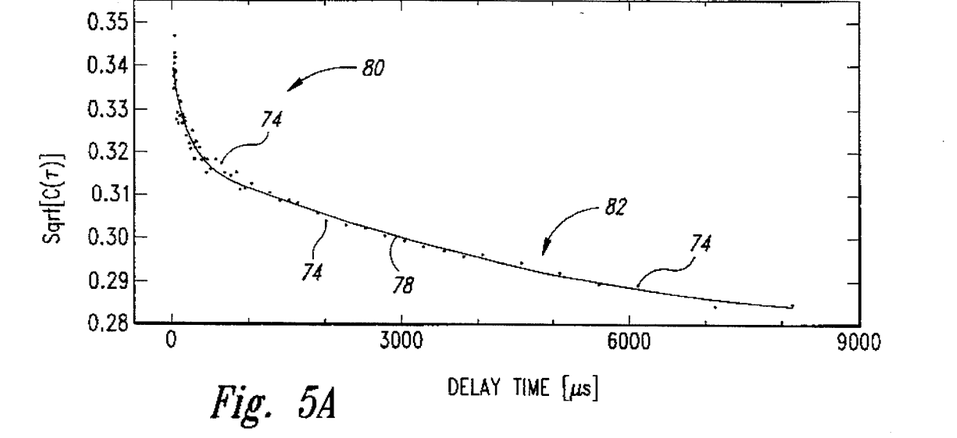
FIG. 5A is a graph of the data using the instrument of FIG. 1 taken from a human lens in vivo.
Figure 5B:
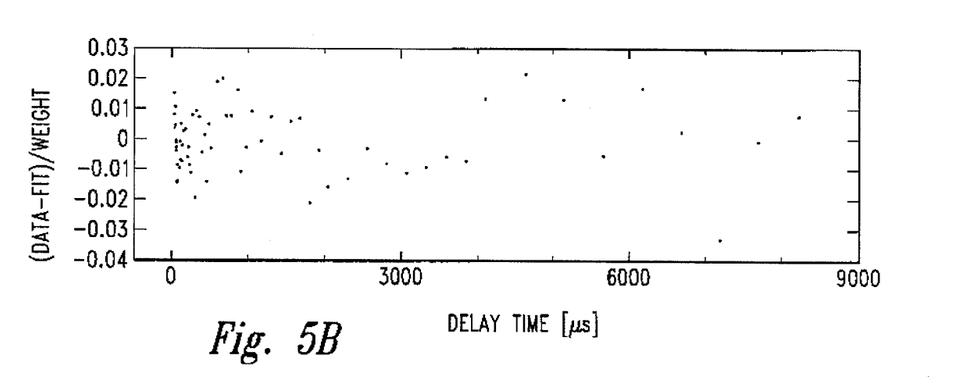
FIG. 5B is a graph of the residual data resulting from the curve fitting of the data of FIG. 5A to a second embodiment of the model autocorrelation function of the present invention.
Figure 5C:
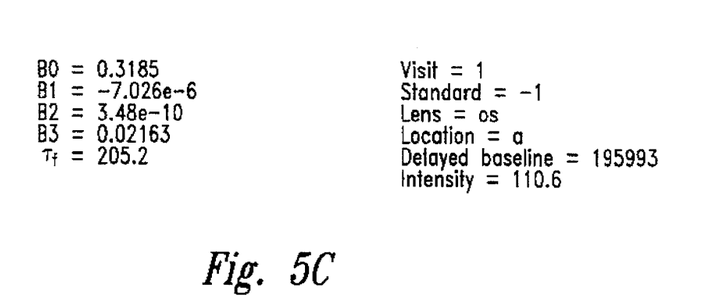
FIG. 5C illustrates the values of the parameters resulting from the curve fitting of the data of FIG. 5A to the inventive model autocorrelation function.

Equation (8) may be recalculated as a square root of the autocorrelation function, as shown in FIG. 5A, by fitting discrete data points 74 to a fitted curve 78 using an equation having the following functional form:

$$z=B_0+B_1*\tau+B_2*\tau^2+B_3*e^{-\tau/\tau_f} \quad (9)$$

where z is the square root of $C_N(\tau)$ in equation (8), $B_0$ is a constant, $B_1$ is the initial slope of a second portion 82 of the fitted curve 78, $B_2$ is indicative of the curvature of the second portion of the fitted curve, $B_3$ is the amplitude of a first portion 80 of the fitted curve 78, due to light scattering from the fast diffusing scatterers, and $\tau_f$ is inversely proportional to the diffusivity of fast scatterers. In addition, equation (9) is a linear equation in four of the five parameters. If the value of $\tau_f$ is known, a simple linear regression may be used to fit the parameters of equation (9) to the discrete data points 74. The residual data are plotted in FIG. 5B. FIG. 5C provides actual values for the five parameters to generate the fitted curve 78 from the discrete data points 74 using the model autocorrelation function of equation (9).

The exponential term in equation (9), $B_3 * e^{-\tau/\tau_f}$, represents a fast decaying first portion 80 of the fitted curve 78. The fast decaying portion 80 of the fitted curve 78 represents the contribution to the intensity of light scattered by fast-diffusing scatterers within the lens 12 (see FIG. 1). The polynomial term in equation (9), $B_0 + B_1 * \tau + B_2 * \tau^2$, represents a second portion 82 of the fitted curve 78. The second portion 82 of the fitted curve 78 represents the cumulative effect of light scattered from slowly diffusing scatterers, immobile scatterers, and elements that give rise to nonexponential characteristics.

The second portion 82 of the fitted curve 78 in FIG. 5A has a positive curvature. However, the second portion 82 may have a negative curvature caused in part by spatial heterogeneity, as discussed above. This corresponds to the oscillatory component of equation (7) having an amplitude greater than zero. It should be noted that the oscillatory component has little or no effect on the fast decaying portion 80 of the fitted curve 78. It should also be noted that, in some individuals, there is no oscillatory component. It is believed that this is due to the fact that there is little or no spatial heterogeneity within the lens 12 (see FIG. 1) or that there is little motion of the lens during the measurement, such that scattering elements do not move in and out of the measurement volume 26 (see FIG. 2) during the measurement period.

Figure 6A:
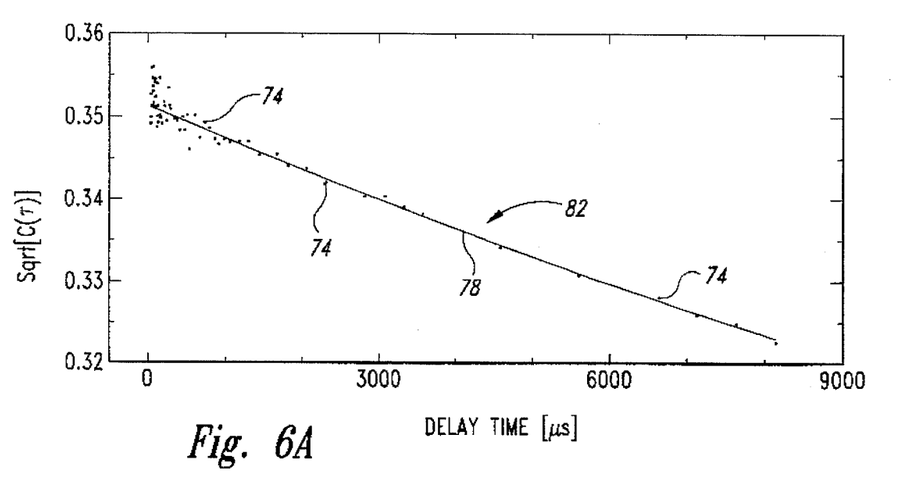
FIG. 6A is a graph of the data using the instrument of FIG. 1 taken from a human lens in vivo.
Figure 6B:
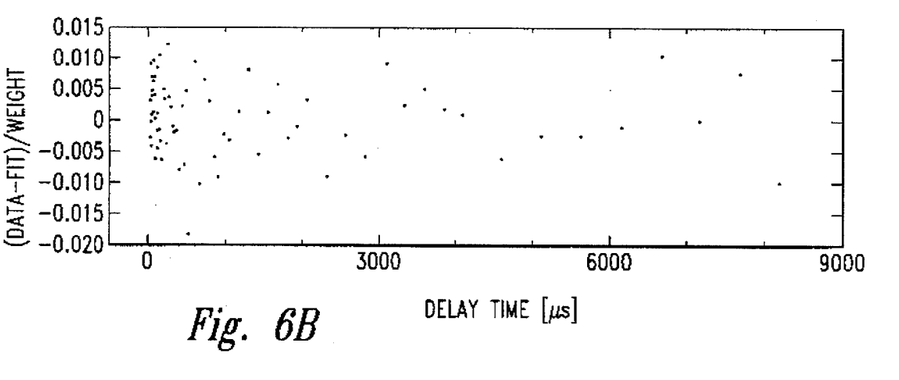
FIG. 6B is a graph of the residual data resulting from the curve fitting of the data of FIG. 6A to the second embodiment of the model autocorrelation function of the present invention.
Figure 6C:
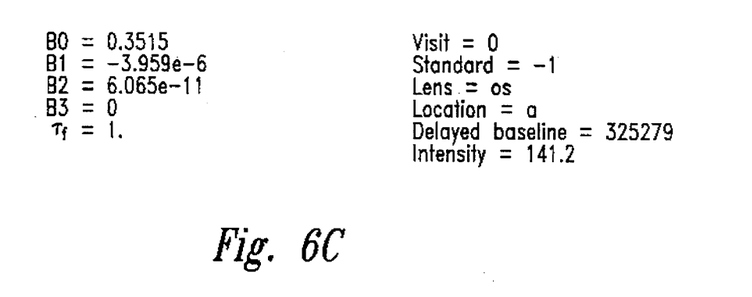
FIG. 6C illustrates the values of the parameters resulting from the curve fitting of the data of FIG. 6A to the inventive model autocorrelation function.

The term $B_2$ in equation (9) can be greater than zero if the second portion 80 of the fitted curve 78 has a positive curvature, such as that shown in FIG. 5A. The term $B_2$ can equal zero if the second portion 70 of the fitted curve 78 is substantially a straight line. This is illustrated in FIG. 6A in which the discrete data points 74 form substantially a straight line. Thus, the fitted curve 78 appears in FIG. 6A as substantially a straight line. The residual data is plotted in FIG. 6B. FIG. 6C provides actual values for the five parameters used to generate the fitted curve 78 from the discrete data points 74. It should be noted that there is no fast decaying portion 80 (see FIG. 5A) in FIG. 6A. This is reflected in the selection of data values for the five parameters shown in FIG. 6C where the value for $B_3$ is zero.

Figure 7A:
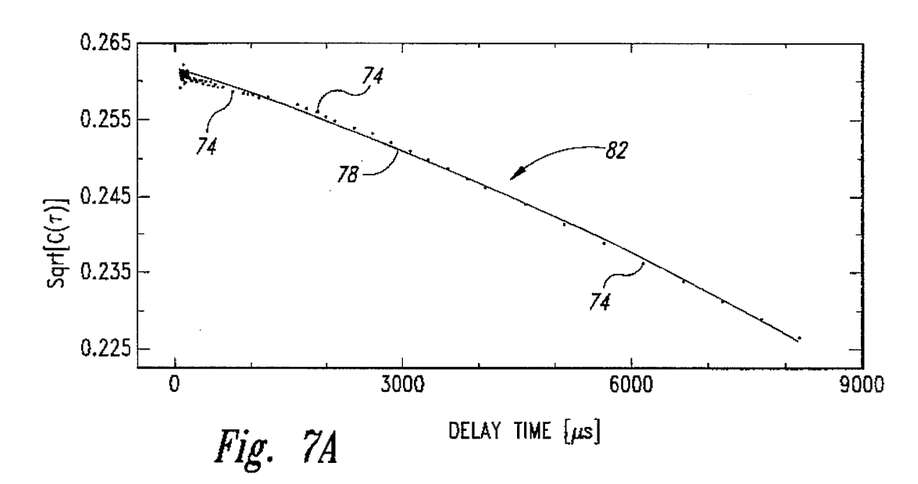
FIG. 7A is a graph of the data using the instrument of FIG. 1 taken from a human lens in vivo.
Figure 7B:
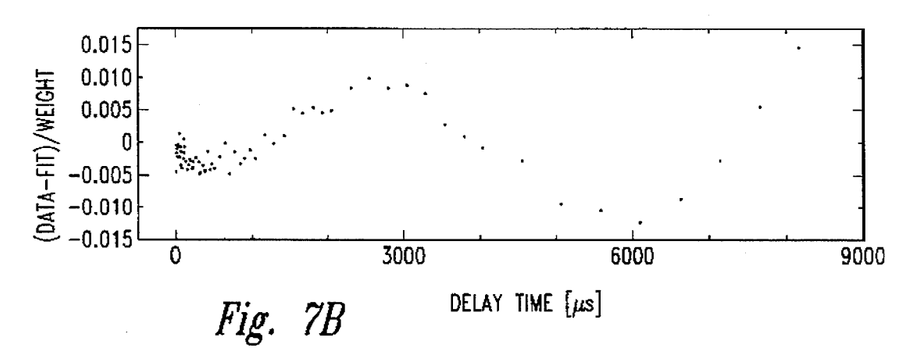
FIG. 7B is a graph of the residual data resulting from the curve fitting of the data of FIG. 7A to the second embodiment of the model autocorrelation function of the present invention.
Figure 7C:
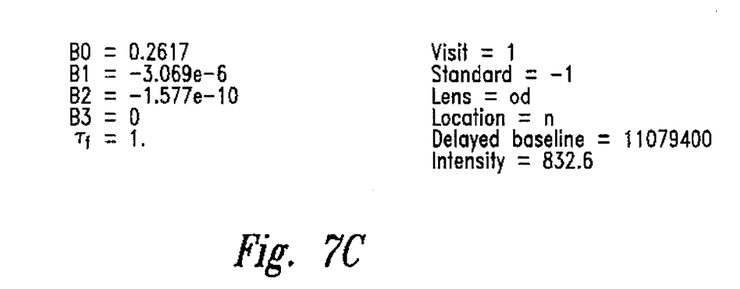
FIG. 7C illustrates the values of the parameters resulting from the curve fitting of the data of FIG. 7A to the inventive model autocorrelation function.

Alternatively, the term $B_2$ can be less than zero if the second portion 82 of the fitted curve 80 has a negative curvature. FIG. 7A provides an example of the second portion 82 of the fitted curve 78 having a negative curvature. The residual data are plotted in FIG. 7B. It should be noted that the residual data plotted in FIG. 7B contains a high frequency sinusoidal pattern. This is attributed to measurement artifact and is ignored by the system 10. FIG. 7C provides actual values for the five parameters used to generate the fitted curve 78 from the discrete data points 74. Again, it should be noted that in FIG. 7A there is no fast decaying portion 80 of the fitted curve 78. This is reflected in the selection of data values for the five parameters shown in FIG. 7C where the value for $B_3$ is zero.

Research has shown that increased cataract development is accompanied by an increase in the spatial heterogeneity within the lens 12 (see FIG. 1). A normal lens 12, with little or no cataract development, has a shape generally illustrated by the fitted curve 78 in FIG. 5A. As cataract development increases, the positive curvature of the second portion 82 of the fitted curve 78 becomes substantially a straight line, such as illustrated in FIG. 6A. This increase in spatial heterogeneity is accompanied by a decrease in the proportion of light scattered by fast diffusing light scatterers within the lens 12. As the cataract development increases, spatial heterogeneity also increases, resulting in the negative curvature illustrated in FIG. 7A. Thus, the evolution of cataractogenesis illustrated in FIGS. 5A, 6A, and 7A illustrates the continuum resulting from the increase in spatial heterogeneity. As previously discussed, the increase in spatial heterogeneity is accompanied by a decrease in the amount of light scattered by fast diffusing scatterers.

The advantage of the model autocorrelation function of the present invention is that all observed characteristics in the discrete data points 74 (see FIG. 5A) can be represented by the five parameters thus minimizing the effects of overdetermination. Tests have shown that the autocorrelation function shown in equations (8) and (9) may be fit to the data collected from a variety of patients, including those with no cataracts, and those having advanced cataract development.

Using the model autocorrelation function of equation (7), the curve fitter 54 (see FIG. 1) must determine a fit in the seven dimensional space of $(f, a_f, a_s, \tau_f, \tau_s, h, \text{ and } \tau_c)$. As those skilled in the art can appreciate, such a determination in seven dimensions is a difficult and time consuming computational task. In contrast, the model autocorrelation function of the present invention, as embodied in equation (9), requires fitting of only five parameters, $B_0, B_1, B_2, B_3$, and $\tau_f$. The curve fitter 54 (see FIG. 1) uses conventional curve fitting algorithms to fit the discrete data points 74 (see FIG. 5A) to the model autocorrelation function of equation (9).

In addition to the difficulty of determining a fit in the seven dimensional space described above, the Marquardt least-squares curve fitting routine must determine a fit with a minimum error in the five dimensional space of $(a_f, a_s, \tau_f, \tau_s, \text{ and } \tau_c)$. A minimization of error in this five dimensional space is also a difficult and time-consuming computational task. In contrast, the model autocorrelation function of equation (9) requires a minimization in only one parameter, $\tau_f$. Thus, the system 10 decreases the computational burden by changing from seven parameters to five parameters, as well as requiring minimization in only one parameter as opposed to minimization in five parameters.

From equation (9) is can be seen that the value of z is linear in the parameters $B_0, B_1, B_2,$ and $B_3$ and is nonlinear only in the parameter $\tau_f$. Minimization of the linear parameters in equation (9) can be easily done using conventional techniques. For any particular value of $\tau_f$, the best fit values of the parameters $B_0, B_1, B_2,$ and $B_3$ can be directly computed using conventional linear regression techniques such as normal equations, singular value decomposition, or the like. To find the best fit values for all five parameters, $B_0, B_1, B_2, B_3$ and $\tau_f$, the curve fitter 54 varies the value of $\tau_f$ in steps of 20 microseconds (μsec) over a range of 20μsec to 1000μsec. This range of values for $\tau_f$ has been found to encompass all subjects in a clinical setting. At each trial value of $\tau_f$, the residual squared errors of the linear regression is computed. The value of $\tau_f$ and the parameters $B_0, B_1, B_2, B_3$ that are associated with the minimum residual sum of squared errors are chosen as the best fit values of $B_0, B_1, B_2, B_3,$ and $\tau_f$.

In the presently preferred embodiment, the system 10 produces seventy one discrete data points 74 (see FIG. 5A).

Thus, for a particular value of $\tau_f$, the coefficients of $B_0$, $B_1$, $B_2$, and $B_3$ can be represented as a seventy one dimensional matrix with four columns. This initial matrix is known as a linear design matrix. The linear design matrix can be manipulated by a number of conventional linear regression techniques to determine the value of the parameters $B_0$, $B_1$, $B_2$, $B_3$, and $\tau_f$ that result in the smallest error.

The system 10 uses Gram-Schmidt QR decomposition of the linear design matrix and a grid search for $\tau_f$. The operation of Gram-Schmidt QR decomposition is well known to those of ordinary skill in the art of modeling and will not be discussed in detail herein. Gram-Schmidt QR decomposition manipulates the linear design matrix into two separate matrices, a Q matrix and an R matrix, to simplify subsequent algebraic calculations. The product of the Q and R matrices are mathematically equivalent to the linear design matrix. Gram-Schmidt QR decomposition is advantageous in that it is not necessary to numerically invert a matrix, as is required by some other forms of linear regression such as normal equations. Another advantage of Gram-Schmidt QR decomposition is that the grid search for $\tau_f$ is simplified because only one inner product need be computed to determine the best value of $\tau_f$.

After the grid search for $\tau_f$ is completed, it is necessary to ensure that the exponential decay embodied in the term $B_3 * e^{-\tau/\tau_f}$ is an appropriate choice for the discrete data points 74 (see FIG. 5A). In certain situations, a value of zero for the parameter $B_3$ may provide a more realistic physical interpretation of the data even though the fitted curve 78 may not fit the discrete data points 74 as accurately. The system 10 sets $B_3$ to zero if any of the following conditions are true:

a. $B_3 < 0$;

b. $\tau_f \leq 20$ μsec or $\tau_f > 1000$ μsec; and c. there is no statistically significant increase in the residual sum of squared errors, as measured by an F test, when $B_3 = 0$.

Thus, the system 10 performs these tests to determine whether the fitted curve 78 can accurately fit the discrete data points 74 if there is no fast decay portion 80 (see FIG. 5A) of the fitted curve. Conventional linear regression may allow the value of $B_3$ to be negative. However, $B_3$ represents the amplitude of the fast diffusing light scatterers. An individual may have a component of light scattering caused by fast diffusing scatterers, or an individual may have no contribution to light scattering from fast diffusing scatterers. However, there is no known condition in which there is a negative contribution to light scattering. Thus, condition "a" above tests for the existence of a negative value. If the linear regression techniques determine a value for $B_3$ that is less than zero, the system sets $B_3$ to zero.

Similarly, the system 10 determines whether the value $\tau_f$, which is inversely proportional to the diffusivity of the diffusivity of fast diffusing mobile scatterers is within a range of values that have physiological significance. A value of $\tau_f$ greater than 1000 μsec or less than 20 μsec is outside the range of any observed autocorrelation functions. Therefore, the system 10 sets the value of $B_3$ to zero if the value of $\tau_f$ is less than or equal to 20 μsec or greater than or equal to 1000 μsec. Finally, the system 10 sets the value of $B_3$ to zero if it determines that the values determined for $B_3$ and $\tau_f$ merely represent some measurement artifact. This determination may be made using conventional statistical analysis, such as an F-test, to determine if there is a statistically significant difference in the residual sum of squared errors using the value for $B_3$ calculated by the system, compared to the residual sum of squared errors when $B_3$ is set to zero.

The model autocorrelation function of equation (9) has five parameters that are shown in the form of one exponential term and one second order polynomial. However, the five parameters could be selected to fit some other model autocorrelation function with equal success. For example, the fast decay portion 80 (see FIG. 5A) of the fitted curve 78 can be modeled with a portion of a straight line, using the formula $y = m\tau + b$, where the slope, m, and the y-intercept, b, are two of the required five parameters. The second portion 82 of the fitted curve 78 can be modeled by a portion of a parabola having the formula $y = A\tau^2 + B\tau + C$, where A is proportional to the curvature of the second portion 82, B is the initial slope of the second portion of the fitted curve, and C is the y-intercept of the second portion. Thus, the model autocorrelation function of the system 10 has five parameters to accurately model the observed characteristics of the autocorrelation data. Those skilled in the art will readily recognize that the particular values for the five parameters will vary depending on the particular form of the model autocorrelation function. Thus, modeling the fast decay portion 80 (see FIG. 5A) will have particular values for the parameters $B_3$ and $\tau_f$ when using the exponential model and a different set of values for the parameters m and b when using the straight line model.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. A system for in vivo inspection of ocular tissue, the system comprising:

a light source producing a light;

an optical system to deliver said light to a selected portion of the ocular tissue;

a collection optical system to collect light scattered by said selected portion of the ocular tissue;

a light detector responsive to said collection optical system to generate signals corresponding to said collected scattered light;

an analyzer coupled to said light detector and constructed to analyze said signals, said analyzer generating a plurality of data points corresponding to the relative intensity of light scattered by scattering elements within said selected portion of the ocular tissue; and a curve fitter to fit said plurality of data points to a predetermined model representative of a light scattering process within the ocular tissue, said predetermined model having the following functional form:

$$C_N(\tau) = F * \{(1 - A_s) * e^{-\tau/\tau_f} + A_s * (1 + C_1 * \tau + C_2 * \tau^2)\}^2$$

where F is amplitude to baseline ratio, $\tau$ is a time delay variable, $\tau_f$ is inversely proportional to the diffusivity of fast scatterers, and $A_s$, $C_1$, and $C_2$ are coefficients that represent the cumulative effect of light scattered from slowly diffusing scatterers, immobile scatterers, and elements that give rise to nonexponential characteristics within the ocular tissue.

2. The system of claim 1 wherein said signals are time varying and said analyzer is further constructed to perform an autocorrelation analysis.

3. A system for in vivo inspection of ocular tissue, the system comprising:

a light source to produce a light;

an optical system to deliver said light to a selected portion of the ocular tissue;

a collection optical system to collect light scattered by said selected portion of the ocular tissue;

a light detector responsive to said collection optical system to generate signals corresponding to said collected scattered light;

an analyzer coupled to said light detector and constructed to analyze said signals, said analyzer generating a plurality of data points corresponding to the relative intensity of light scattered by scattering elements within said selected portion of the ocular tissue; and a curve fitter to fit said plurality of data points to a predetermined model autocorrelation function representative of a light scattering process within the ocular tissue, said model autocorrelation function having first and second curve portions and having the following functional form:

$$z = B_0 + B_1*\tau + B_2*\tau^2 + B_3*e^{-\tau/\tau_f}$$

where $B_0$ is a constant indicative of a z-intercept of said second portion, $B_1$ is an initial slope of said second portion, $B_2$ is indicative of a curvature of said second portion, $B_3$ is an amplitude of the said first portion, $\tau$ is a time delay variable, and $\tau_f$ is inversely proportional to a diffusivity of fast scatterers within the ocular tissue.

4. A system for in vivo inspection of ocular tissue, the system comprising:

a light source producing light;

an optical system to deliver said light to the ocular tissue;

a collection optical system to collect light scattered by the ocular tissue;

a light detector responsive to said collection optical system to generate signals corresponding to said collected scattered light;

an analyzer coupled to said light detector and constructed to analyze said signals, said analyzer generating a plurality of data points corresponding to the relative intensity of light scattered by scattering elements within the ocular tissue; and a curve fitter to fit said plurality of data points to a predetermined model representative of a light scattering process within the ocular tissue and generate a fitted curve having first and second portions, said predetermined model having an exponential term representing said first portion and a polynomial term representing said second portion.

5. The system of claim 4 wherein said signals are time varying and said analyzer is further constructed to perform an autocorrelation analysis.

6. The system of claim 4 wherein said curve fitter is further constructed to fit said first portion to said exponential term having the following form:

$$(1-A_s)*e^{-\tau/\tau_f}$$

where $A_s$ is a coefficient representative of the cumulative effect of light scattered from slowly diffusing scatterers, immobile scatterers, and elements that give rise to nonexponential characteristics within the ocular tissue, $\tau$ is a time delay variable, and $\tau_f$ is inversely proportional to the diffusivity of fast diffusing mobile scatterers.

7. The system of claim 4 wherein said curve fitter is further constructed to fit said second portion to said polynomial term having the following form:

$$A_s*(1+C_1*\tau+C_2=\tau^2)$$

where $\tau$ is a time delay variable, and $A_s$, $C_1$, and $C_2$ are coefficients that represent the cumulative effect of light scattered from slowly diffusing scatterers, immobile scatterers, and elements that give rise to nonexponential characteristics within the ocular tissue.

8. A system for in vivo inspection of ocular tissue, the system comprising:

a light source producing a light;

an optical system to deliver said light to the ocular tissue;

a collection optical system to collect light scattered by the ocular tissue;

a light detector responsive to said collection optical system to generate signals corresponding to an intensity of said collected scattered light;

an analyzer coupled to said light detector and constructed to analyze said signals, said analyzer generating a plurality of data points corresponding to said intensity of light scattered by scattering elements within the ocular tissue; and a curve fitter to fit said plurality of data points to a predetermined model representative of a light scattering process within the ocular tissue and to generate a fitted curve having first and second portions and only five parameters representing said first and second portions, said first portion being represented by two of said five parameters and said second portion being represented by the remaining three of said five parameters.

9. The system of claim 8 wherein said curve fitter is further constructed to fit said first portion to a substantially straight line having the following functional form:

$$y = m\tau + b$$

where m is the slope of said straight line, and b is the y-intercept of said straight line, where m and b are said two of said five parameters.

10. The system of claim 8 wherein said curve fitter is further constructed to fit said second portion to a portion of a parabola, represented by said remaining three of said five parameters and having the following functional form:

$$y = A\tau^2 + B\tau^* + C$$

where A is proportional to the curvature of said parabola portion, B is the initial slope of said parabola portion, and C is the y-intercept of said parabola portion, where A, B, and C are said remaining three of said five parameters.

11. A method for the in vivo inspection of ocular tissue, the method comprising the steps of:

generating a light;

delivering said light to the ocular tissue;

collecting light scattered by the ocular tissue;

generating signals corresponding to an intensity of said collected scattered light;

generating a plurality of data points corresponding to said intensity of light scattered by scattering elements within the ocular tissue; and fitting said plurality of data points to a predetermined model representative of a light scattering process within the ocular tissue to generate a fitted curve having first and second portions, said predetermined model having an exponential term representing said first portion and a polynomial term representing said second portion.

12. The method of claim 11 wherein said predetermined model has the following functional form:

$$C_N(\tau) = F * \{(1-A_s)*e^{-\tau/\tau_f} + A_s*(1+C_1*\tau+C_2*\tau^2)\}^2$$

where F is amplitude to baseline ratio, $\tau$ is a time delay variable, $\tau_f$ is inversely proportional to the diffusivity of fast scatterers, and $A_s$, $C_1$, and $C_2$ are coefficients that represent the cumulative effect of light scattered from slowly diffusing scatterers, immobile scatterers, and elements that give rise to nonexponential characteristics within the ocular tissue.

13. The method of claim 11 wherein said model autocorrelation function has the following functional form:

$$z = B_0 + B_1\tau * + B_2*\tau^2 + B_3*e^{-\tau/\tau_f}$$

where $B_0$ is the z-intercept of said second portion, $B_1$ is an initial slope of said second portion, $B_2$ is indicative of a curvature of said second portion, $B_3$ is an amplitude of the said first portion, $\tau$ is a time delay variable, and $\tau_f$ is inversely proportional to a diffusivity of fast scatterers within the ocular tissue.

14. The method of claim 11 wherein said exponential term has the following form:

$$(1-A_s)*e^{-\tau/\tau_f}$$

where $A_s$ is a coefficient representative of the cumulative effect of light scattered from slowly diffusing scatterers, immobile scatterers, and elements that give rise to nonexponential characteristics within the ocular tissue, $\tau$ is a time delay variable, and $\tau_f$ is inversely proportional to the diffusivity of fast diffusing mobile scatterers.

15. The method of claim 11 wherein said polynomial term has the following form:

$$A_s*(1+C_1*\tau+C_2*\tau^2)$$

where $\tau$ is a time delay variable, and $A_s$, $C_1$, and $C_2$ are coefficients that represent the cumulative effect of light scattered from slowly diffusing scatterers, immobile scatterers, and elements that give rise to nonexponential characteristics within the ocular tissue.

16. A method for the in vivo inspection of ocular tissue, the method comprising the steps of:

generating a light;

delivering said light to the ocular tissue;

collecting light scattered by the ocular tissue;

generating signals corresponding to an intensity of said collected scattered light;

generating a plurality of data points corresponding to said intensity of light scattered by scattering elements within the ocular tissue; and fitting said plurality of data points to a predetermined model representative of a light scattering process within the ocular tissue to generate a fitted curve having first and second portions and only five parameters representing said first and second portions, said first portion being represented by two of said five parameters and said second portion being represented by the remaining three of said five parameters.

17. The method of claim 16 wherein said first portion is modeled by a straight line having the following functional form:

$$y = m\tau + b$$

where m is the slope of said straight line, and b is the y-intercept of said straight line, where y and b are said two of said five parameters.

18. The method of claim 16 wherein said second portion is modeled by a portion of a parabola represented by said remaining three of said five parameters to represent said parabola portion and having the following functional form:

$$y = A\tau^2 + BT + C$$

where A is Proportional to the curvature of said parabola portion, B is the initial slope of said parabola portion, and C is the y-intercept of said parabola portion.

* * * * *

UNITED STATES PATENT AND TRADEMARK OFFICE
CERTIFICATE OF CORRECTION

PATENT NO.     : 5,542,422
DATED          : August 6, 1996
INVENTOR(S)    : Douglas L. Hayden It is certified that error appears in the above identified patent and that said Letters Patent is hereby corrected as shown below:

In column 13, claim 7, line 66, please delete "$A_*\ast(1+C_1\ast\tau+C_2=\tau^2)$" and insert therefor --$A_*\ast(1+C_1\ast\tau+C_2\ast\tau^2)$--.

In column 15, claim 13, line 12, please delete "$z=B_0+B_1\tau\ast+B_2\ast\tau^2+B_3\ast e^{-\tau/\tau}f$" and insert therefor --$z=B_0+B_1\ast\tau+B_2\ast\tau^2+B_3\ast e^{-\tau/\tau}f$--.

In column 16, claim 18, line 35, please delete "$y=A\tau^2+BT+C$" and insert therefor --$y=A\tau^2+B\tau+C$--.

In column 16, claim 18, line 36, please delete "Proportional" and insert therefor --proportional--.

Signed and Sealed this

Twelfth Day of November, 1996

*Attest:*

BRUCE LEHMAN

*Attesting Officer*     *Commissioner of Patents and Trademarks*